US00PP24954P2

(12) United States Plant Patent
Huisman

(10) Patent No.: US PP24,954 P2
(45) Date of Patent: Oct. 7, 2014

(54) ***CLEMATIS* PLANT NAMED 'OVATION'**

(50) Latin Name: ***Clematis* hybrid**
Varietal Denomination: Ovation

(71) Applicant: Nico Huisman, Boskoop (NL)

(72) Inventor: Nico Huisman, Boskoop (NL)

( * ) Notice: Subject to any disclaimer, the term of this patent is extended or adjusted under 35 U.S.C. 154(b) by 94 days.

(21) Appl. No.: 13/694,202

(22) Filed: Nov. 6, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

GTITM UPOVROM Citation for 'Ovation' as per QZ PBR 20110098; Feb. 1, 2011.*

* cited by examiner

*Primary Examiner* — Kent L Bell
(74) *Attorney, Agent, or Firm* — Penny J. Aguirre

(57) ABSTRACT

A new cultivar of *Clematis* named 'Ovation', characterized by its compact, outward spreading plant habit, its abundant and relatively large white flowers, and its dark green leaves.

2 Drawing Sheets

Botanical classification: *Clematis* hybrid.
Variety denomination: 'Ovation'.

BACKGROUND OF THE INVENTION

The present invention relates to a new and distinct cultivar of *Clematis* of hybrid origin and will be referred to hereafter by its cultivar name 'Ovation'. 'Ovation' is grown for use in the landscape or as a flowering potted plant for the terrace.

'Ovation' was derived from a controlled cross made by the Inventor in Boskoop, The Netherlands in spring of 2004 between the female parent, an unnamed plant of *Clematis marmoraria* and the male parent, *Clematis×cartmanii* 'Lunar Lass' (not patented). 'Ovation' was selected in summer of 2006 as a single unique plant amongst the seedlings of the above cross.

Asexual reproduction of the new cultivar was first accomplished by internodial stem cuttings under the direction of the inventor in Boskoop, The Netherlands in 2003. The characteristics of this cultivar have been determined to be stable and are reproduced true to type in successive generations.

SUMMARY OF THE INVENTION

The following traits have been repeatedly observed and represent the characteristics of the new cultivar as grown outdoors in Boskoop, The Netherlands. These attributes in combination distinguish 'Ovation' from other cultivars of *Clematis* known to the Inventor.

1. 'Ovation' exhibits a compact, outward spreading plant habit.
2. 'Ovation' exhibits abundant relatively large white flowers.
3. 'Ovation' exhibits dark green leaves.

The female parent of 'Ovation', an unnamed plant of *Clematis marmoraria*, differs from 'Ovation' in having an even more compact and prostrate plant habit, in having smaller flowers, and in having lighter green leaves. The male parent of 'Ovation', 'Lunar Lass' differs from 'Ovation' in having a climbing plant habit, in having smaller flowers, and in having light green leaves. 'Ovation' can also be compared to cultivars of *Clematis×cartmanii*; 'Blaaval' (not patented, also known as 'Avalanche') and 'Joe' (not patented). 'Blaaval' differs from 'Ovation' in having larger flowers, larger leaves, and a climbing plant habit. 'Joe' differs from 'Ovation' most significantly in having a climbing plant habit.

BRIEF DESCRIPTION OF THE DRAWING

The accompanying colored photographs illustrate the overall appearance and distinct characteristics of the new *Clematis*. The photographs were taken of a two year-old plant of 'Ovation' as grown in a two-liter container in Boskoop, The Netherlands.

The photograph in FIG. 1 shows the habit in bloom.

Figure 1:
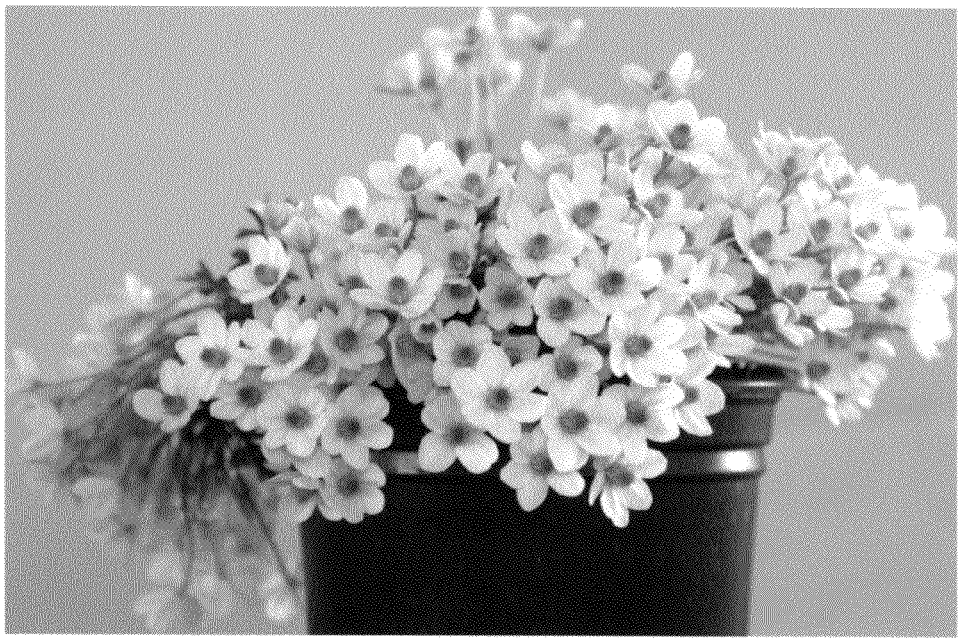
Figure 2:
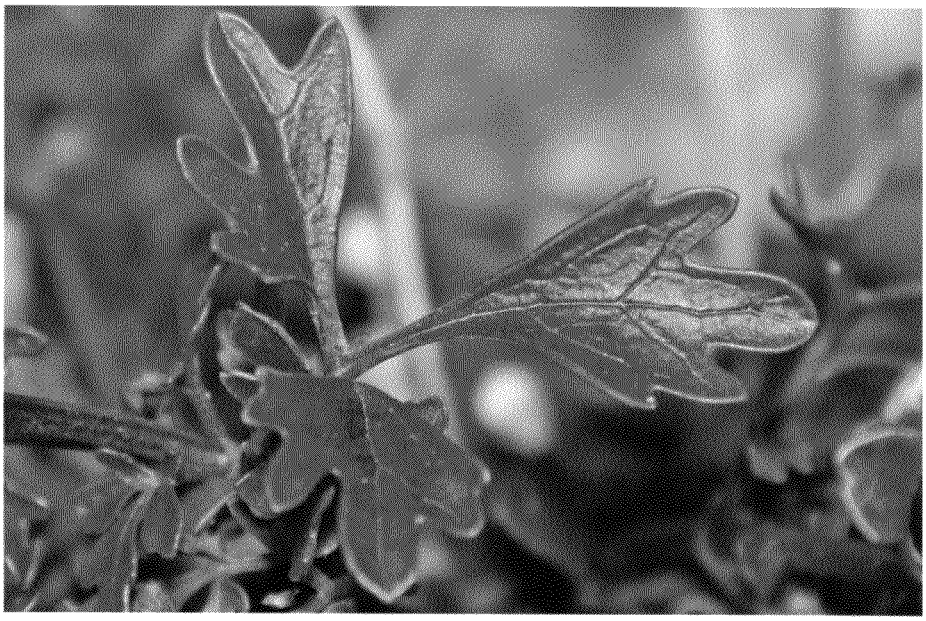

The photograph in FIG. 2 provides a close-up view of the foliage.

The colors in the photographs are as close as possible with the digital photography techniques available, the color values cited in the detailed botanical description accurately describe the colors of the new *Clematis*.

DETAILED BOTANICAL DESCRIPTION

The following is a detailed description of two year-old plants as grown outdoors in two-liter containers in an unheated greenhouse in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms for 4 to 6 weeks in spring in The Netherlands.

*Plant type*.—Evergreen shrub.

*Plant habit*.—Compact, outward spreading.

*Height and spread*.—Average of 12 cm in height and 30 cm in width.

*Cold hardiness*.—At least to U.S.D.A. Zone 7.

*Diseases*.—No susceptible or resistance to diseases has been observed.

*Root description*.—Fleshy.

*Propagation*.—Internodial softwood cuttings from vegetative shoots.

*Growth rate*.—Low to moderately vigorous.

Stem description:

*Shape*.—Round.

*Stem color*.—Between 200A and 202A.

*Stem size*.—Average of 14, 6.6 cm in length, 1.5 mm in diameter.

*Stem surface*.—Moderately glossy and covered with short hairs, average length 0.7 mm in length.

*Stem strength*.—Strong.

*Stem aspect*.—Spreading to creeping to upright (near vertical).

*Internode length*.—2.5 cm in length.

*Branching*.—Moderately branching, main stems grow directly from the base.

Foliage description:

*Leaf arrangement*.—Opposite.

*Leaf division*.—Compound.

*Leaf shape*.—Trifoliate, hastate in outline.

*Leaf base*.—Hastate.

*Leaf apex*.—Acute.

*Leaf size*.—Average of 3.1 cm in length and 3.2 cm in width.

*Leaflet shape*.—Three-loped, ovate in outline.

*Leaflet base*.—Attenuate.

*Leaflet apex*.—Acute.

*Leaflet venation*.—Pinnate, upper surface; between N137C to N137D and 147A, lower surface; 147B.

*Leaflet margins*.—Sparsely serrate.

*Leaflet attachment*.—Leaflets petioluled with leaf petioled, 1.4 cm in length and 1.5 mm in diameter round in shape.

*Leaflet surface*.—Leathery, slightly glossy and glabrous on both surfaces.

*Leaflet size*.—Average of 2.2 cm in length and 1.4 cm in width.

*Leaflet color*.—Young upper surface; 137B, young lower surface; 147B, mature upper surface; between N137C to N137D and 147A, mature lower surface; 147B.

*Petiole and petiolules*.—Petioles about 1.4 cm in length and 1.5 mm in diameter, petiolules about 1 cm in length and 1.5 mm in diameter, petioles and petiolules; flattened rounded in shape, 146A to 147A in color, surface moderately glossy and covered with short hairs an average of 0.7 mm in length.

Inflorescence description:

*Inflorescence type*.—Axillary and terminal cyme.

*Inflorescence size*.—Average of 7 cm in height and 5 cm in width.

*Peduncles*.—Average of 1.9 cm in length and 1.5 mm in diameter, 146A to 146B in color, surface glabrous.

*Pedicels*.—Average of 4.1 cm in length and 1 mm in diameter, moderately strong, 144B in color, main flower in a cyme in an average angle of 0° (=straight on top of peduncle), secondary flowers in a cyme in an average angle of 45°, surface glabrous.

*Flower bud*.—Held outward to upright, obovate in shape, about 0.7 cm in length and 0.5 cm in diameter, 144D in color.

*Flower fragrance*.—Faint, fresh and slightly minty.

*Lastingness of flowers*.—Average of 10 days.

*Flower quantity*.—Average of 5 per inflorescence, 450 per plant as grown in a two-liter container.

*Flower type*.—Single, rotate, spreading.

*Flower aspect*.—Outward to upright.

*Flower size*.—Average of 2.8 cm in diameter and 1.0 cm in depth.

*Tepal number*.—Average of 5.

*Tepal shape*.—Obovate.

*Tepal apex*.—Obtuse.

*Tepal base*.—Cuneate.

*Tepal margins*.—Entire.

*Tepal surface*.—Upper surface; glabrous, lower surface and margins; slightly covered moderately pubescent with soft short hairs an average of 1 mm in length and 157D in color.

*Tepal color*.—Upper surface when opening; 145D, base 145B to 145C, lower surface when opening; 145D, base 145B to 145C, upper surface fully opened, 157D, base 145D, lower surface fully opened; 157D, base 145D.

*Tepal size*.—Average of 1.4 cm in length and 0.9 cm in width.

Reproductive organs:

*Gynoecium*.—Numerous pistils (about 50), 5 mm in length, stigma is club-shaped and 144C in color, style is 4.9 mm in length and 144A to 144B in color, ovary is 144A in color with a bundle of soft hairs at the base of each ovary; average of 4.5 mm in length and NN155D in color with a strong silvery shine.

*Androecium*.—Average of 12 stamens, filaments are 5 mm in length, narrow obovate in shape and 145A in color, anthers are 1 mm in length, basifixed, narrow oblong in shape and 150B to 150C in color, pollen is low in quantity and too minimal to be measured with RHS-CC.

*Seed/fruit*.—No seed or fruit detected to date.

It is claimed:

1. A new and distinct cultivar of *Clematis* plant named 'Ovation' as herein illustrated and described.

* * * * *